United States Patent
Sorrenti et al.

(10) Patent No.: US 8,679,129 B2
(45) Date of Patent: Mar. 25, 2014

(54) AUTOMATIC LOCKING CASPER DISTRACTOR

(75) Inventors: Michael Sorrenti, Middleboro, MA (US); Douglas Raymond, Randolph, MA (US); David Konieczynski, Needham, MA (US); Ed Zalenski, Lakeville, MA (US); Conor McRea, Dedham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/474,321

(22) Filed: May 17, 2012

(65) Prior Publication Data

US 2012/0226284 A1     Sep. 6, 2012

Related U.S. Application Data

(62) Division of application No. 11/581,640, filed on Oct. 16, 2006, now Pat. No. 8,197,488.

(51) Int. Cl.
*A61B 17/66* (2006.01)

(52) U.S. Cl.
USPC ........................................................ 606/90

(58) Field of Classification Search
USPC ........... 606/60, 61, 69, 70–74, 86 A, 90, 102, 606/105, 246–279, 280–299
See application file for complete search history.

(56) References Cited

U.S. PATENT DOCUMENTS

| 5,776,197 | A | 7/1998 | Rabbe et al. |
| 6,017,342 | A | 1/2000 | Rinner |
| 6,139,493 | A | 10/2000 | Koros et al. |
| 6,159,214 | A | 12/2000 | Michelson |
| 6,648,891 | B2 | 11/2003 | Kim |
| 6,709,389 | B2 | 3/2004 | Farascioni |
| 7,004,947 | B2 | 2/2006 | Shluzas et al. |
| 7,011,658 | B2 | 3/2006 | Young |
| 7,087,084 | B2 | 8/2006 | Reiley |
| 7,226,451 | B2 | 6/2007 | Shluzas et al. |
| 7,494,463 | B2 | 2/2009 | Nehls |
| 7,522,953 | B2 | 4/2009 | Kaula et al. |
| 7,547,318 | B2 | 6/2009 | Birkmeyer et al. |
| 2004/0204710 | A1 | 10/2004 | Patel et al. |
| 2004/0230191 | A1* | 11/2004 | Frey et al. ................ 606/57 |
| 2005/0021040 | A1 | 1/2005 | Bertagnoli |

(Continued)

FOREIGN PATENT DOCUMENTS

| CA | 2534103 | 4/2005 |
| WO | 0021442 A1 | 4/2000 |

(Continued)

*Primary Examiner* — Christopher Beccia

(74) *Attorney, Agent, or Firm* — Maginot, Moore & Beck, LLP

(57) ABSTRACT

A vertebral distractor system includes a crossbar and a first distractor arm having a first end portion coupled to the crossbar and a second end portion with a first bore configured to axially receive a first coupling portion of a first pin. A second distractor arm includes a third end portion coupled to the crossbar and a fourth end portion with a second bore configured to receive a second coupling portion of a second pin. A first pin locking mechanism is configured to couple the first coupling portion and the first distractor arm within the first bore such that when the first coupling portion and the first distractor arm are coupled, movement of the first pin outwardly of the first bore is not allowed.

8 Claims, 8 Drawing Sheets

(56) References Cited

U.S. PATENT DOCUMENTS

| | | |
|---|---|---|
| 2005/0203533 A1 | 9/2005 | Ferguson et al. |
| 2006/0084844 A1 | 4/2006 | Nehls |
| 2006/0247649 A1* | 11/2006 | Rezach et al. .................. 606/90 |
| 2008/0177270 A1 | 7/2008 | Sorrenti et al. |

FOREIGN PATENT DOCUMENTS

| | | |
|---|---|---|
| WO | 03024344 A1 | 3/2003 |
| WO | 2005009209 A2 | 2/2005 |
| WO | 2005099589 A1 | 10/2005 |
| WO | 2006058221 A2 | 6/2006 |

* cited by examiner

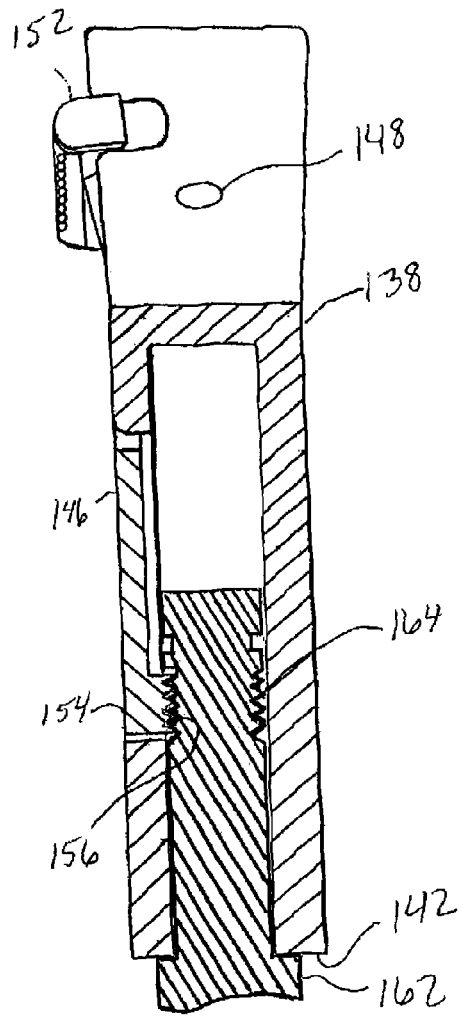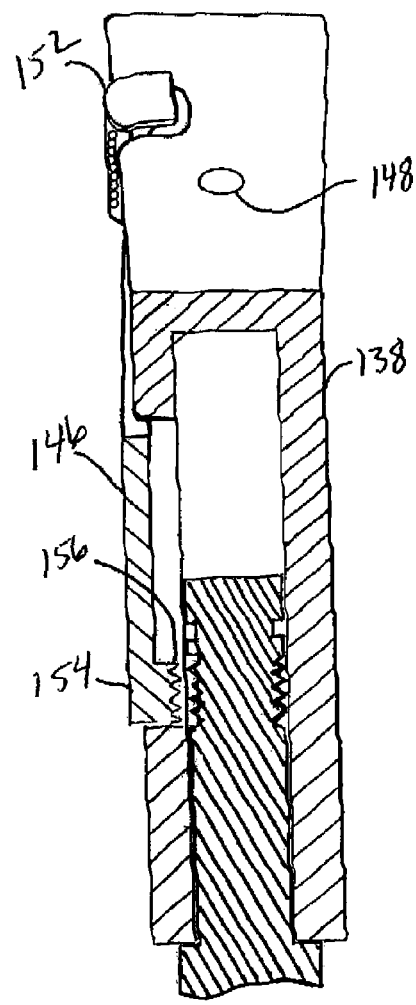
FIG. 6
FIG. 7

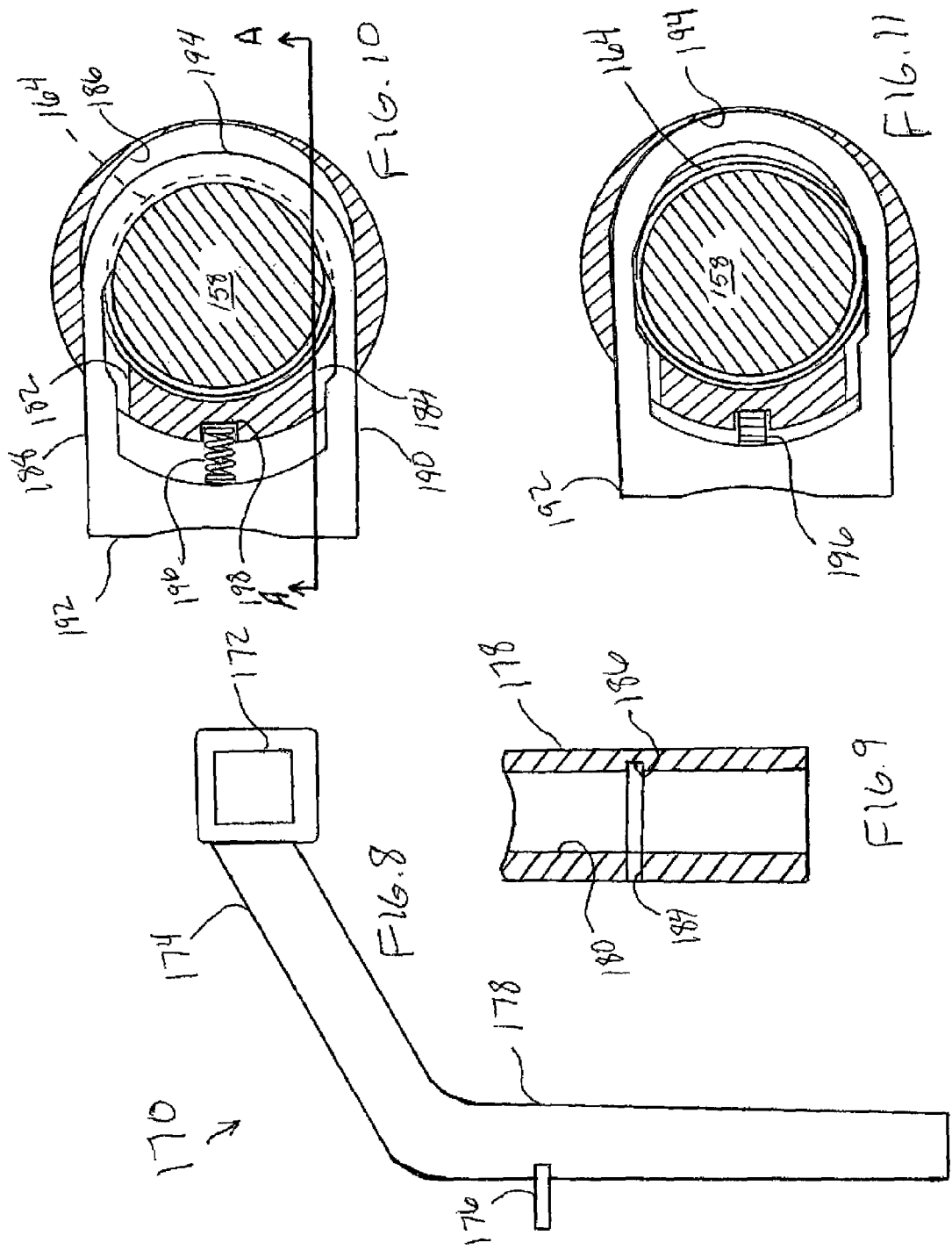

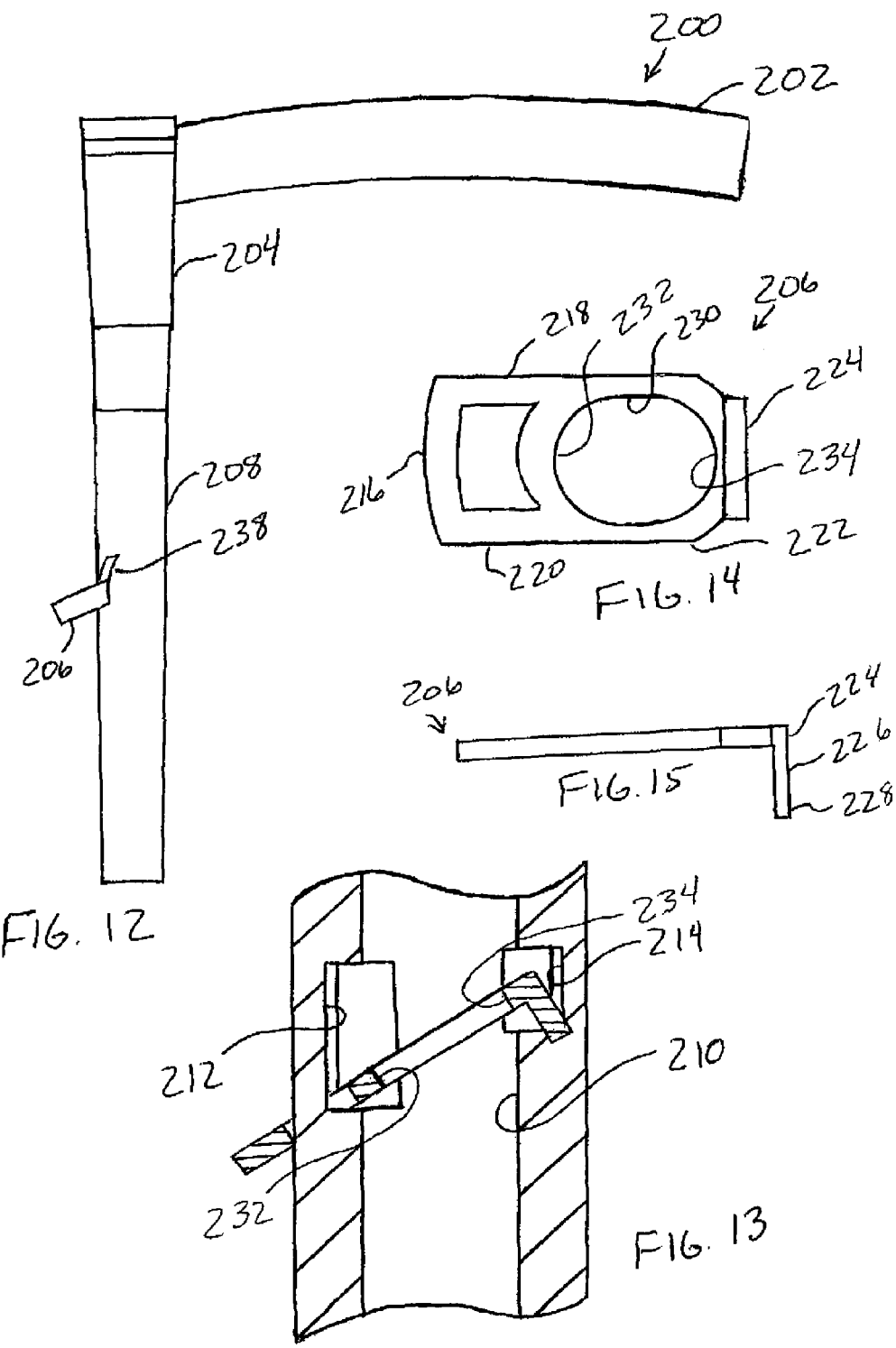

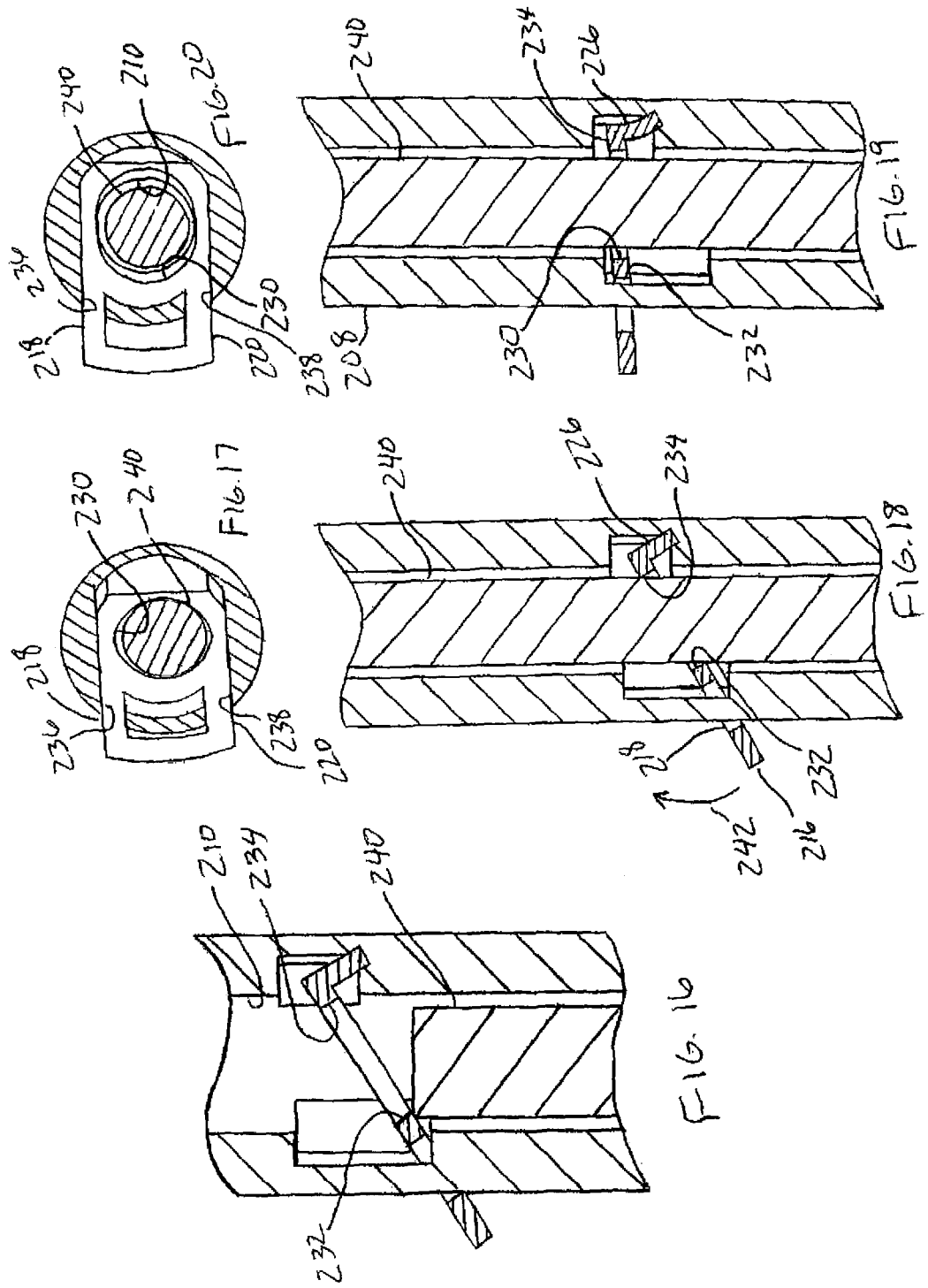

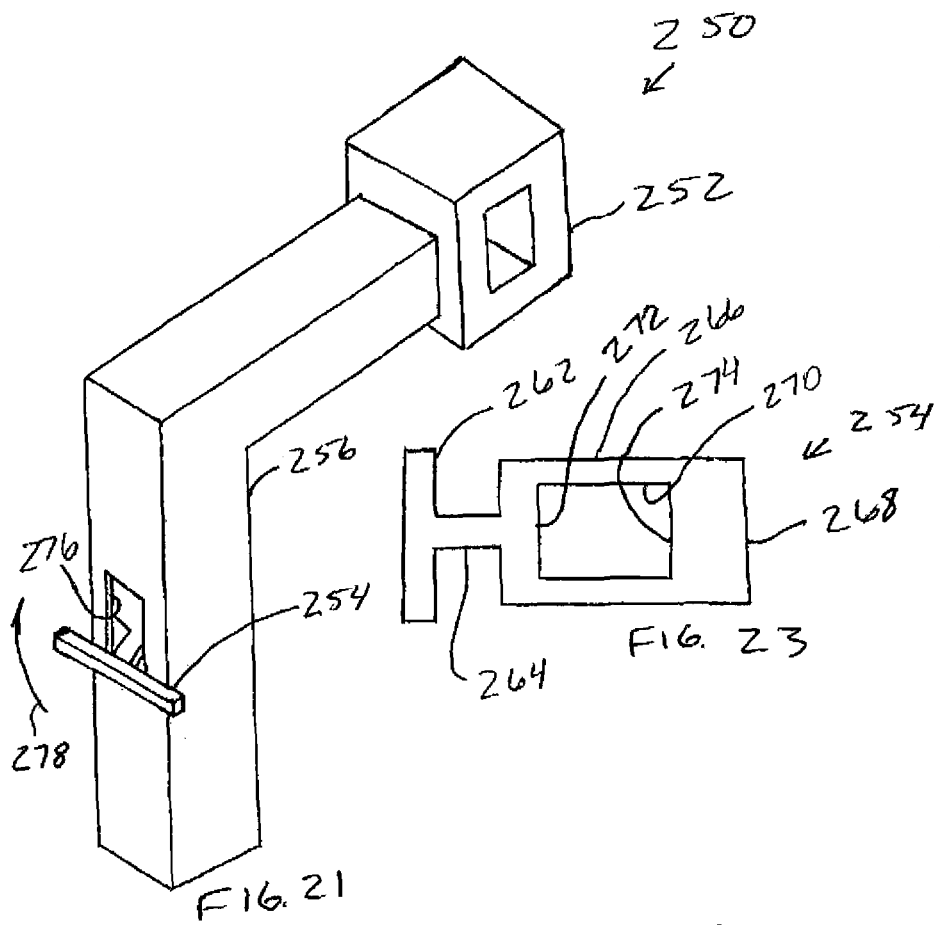
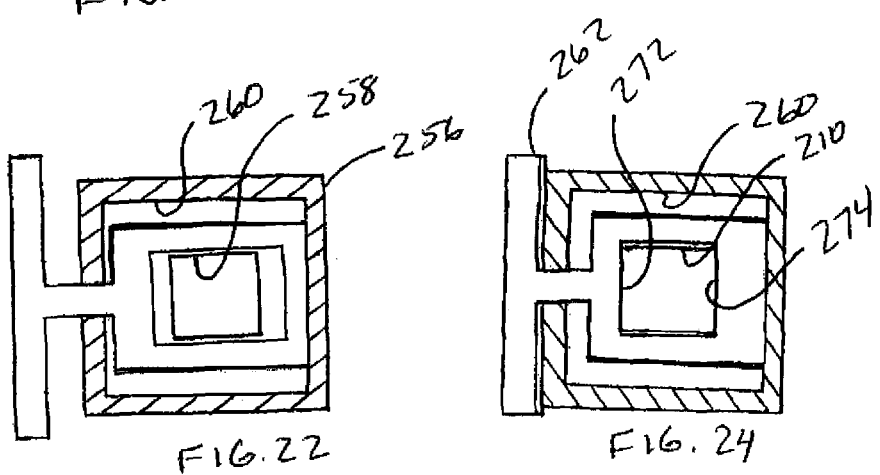

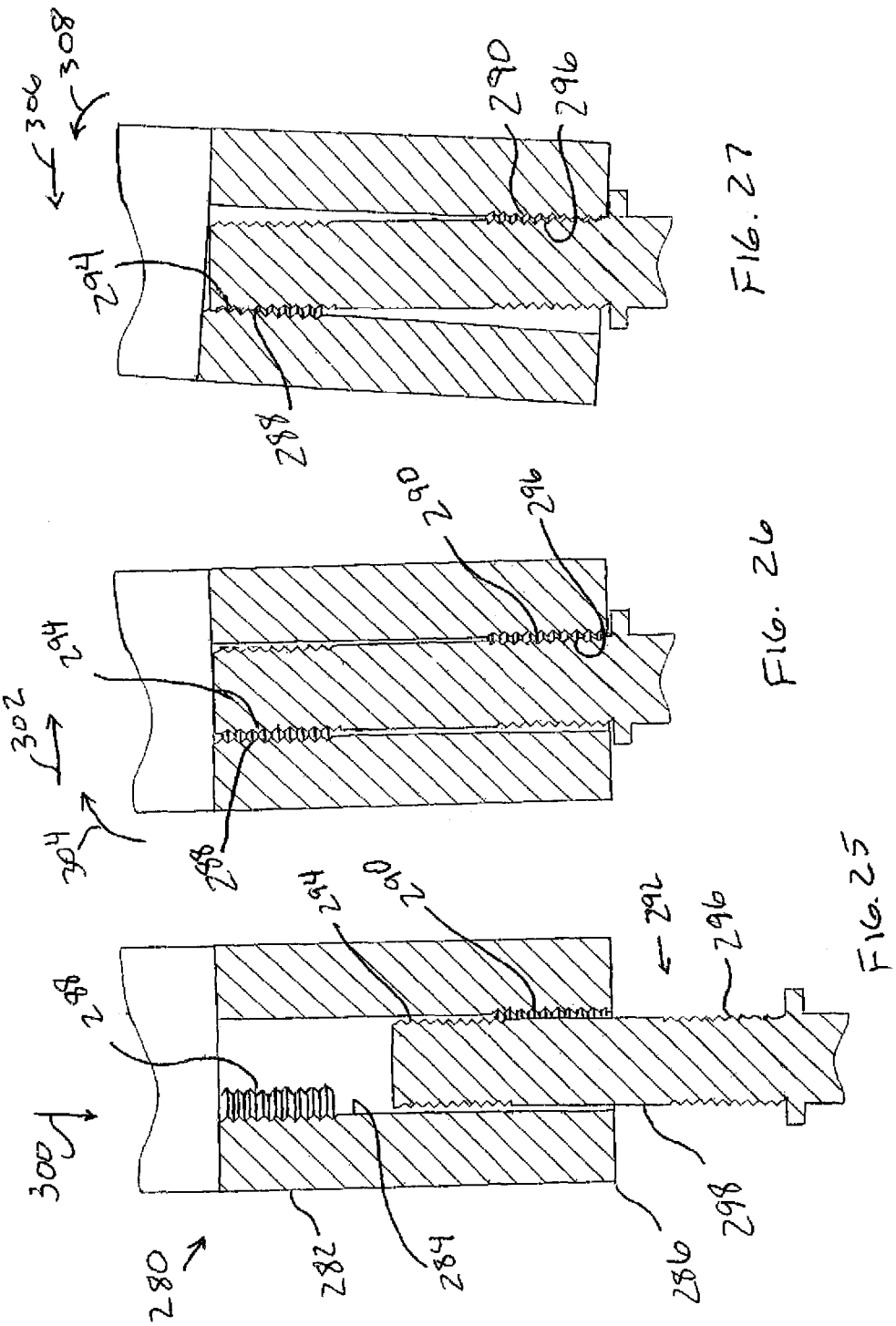

_US 8,679,129 B2_

AUTOMATIC LOCKING CASPER DISTRACTOR

This application is a divisional of application Ser. No. 11/581,640, filed on Oct. 16, 2006, which issued as U.S. Pat. No. 8,197,488 on Jun. 12, 2012, the disclosure of which is herein totally incorporated by reference in its entirety.

FIELD OF THE INVENTION

This invention relates to surgical devices and, more particularly, to devices used to facilitate surgery of vertebral bodies.

BACKGROUND

Spinal surgery often requires removal of the existing intervertebral disc tissue located between adjacent vertebrae and replacement thereof with an intervertebral implant which may take the form of a cage or other fusion device or an artificial disc which may be of the type which allows movement of the adjacent vertebrae with respect to each other.

In any event, it is necessary to initially separate the adjacent vertebrae from each other and to retain them apart during the surgical procedure to clear out the existing disc tissue, perform a spinal decompression, prepare the bony endplates to receive the implant, and insert the intervertebral implant.

It has been known heretofore to distract adjacent vertebrae away from each other using an instrument having a pair of anchor pins, one pin anchored in each of the adjacent vertebrae, wherein one anchor pin is received in a tube that is fixedly attached to a crossbar and the other pin is received in a tube that is movably attached to the crossbar. Thus, by moving the movable tube away from the fixed tube, adjacent vertebrae are forced away from each other or distracted. Typically, the crossbar is located some distance away from the vertebrae being distracted. This results in a moment arm at the point where the tubes are coupled to the crossbar. Because the anchor pins are solidly embedded in the vertebrae, the moment arm causes the upper portion of the tubes to move farther apart from each other than the lower portion of the tubes. The resultant force operates to slide the tubes upwardly on the pins away from the vertebrae until one or both of the anchor pins are no longer fully engaged within the tubes. Manipulation and impaction of instruments during the surgical procedure can also exacerbate this relative movement of the pins within the tubes.

A need exists for a mechanism which restricts the movement of the distractor tubes away from the vertebrae when the distractor is in use. A further need exists for a distractor which restricts movement of the distractor tubes away from the vertebrae which is easily manipulated during a surgical procedure. It would be advantageous if the distractor could be coupled to the anchor pins using a mechanism that is mounted on the distractor. It would be beneficial if this mechanism were automatic and did not require active engagement by the user, thus simplifying surgical use. Moreover, it would be beneficial if the anchor pins could be coupled to the distractor without the need for the anchor pins to extend above the distractor tubes.

SUMMARY

A vertebral distractor system and method is disclosed. In accordance with one embodiment according to the invention a vertebral distractor system includes a crossbar and a first distractor arm having a first end portion coupled to the crossbar and a second end portion with a first bore configured to axially receive a first coupling portion of a first pin. A second distractor arm includes a third end portion coupled to the crossbar and a fourth end portion with a second bore configured to receive a second coupling portion of a second pin. A first pin locking mechanism is configured to couple the first coupling portion and the first distractor arm within the first bore such that when the first coupling portion and the first distractor arm are coupled, movement of the first pin outwardly of the first bore is not allowed.

In accordance with another embodiment, a vertebral distractor assembly includes a crossbar with a first distractor arm having a first end portion coupled to the crossbar and a second end portion with a first bore configured to receive a first coupling portion of a first pin. Additionally, a second distractor arm has a third end portion coupled to the crossbar and a fourth end portion with a second bore configured to receive a second coupling portion of a second pin. The assembly further includes an automatic locking mechanism with an engagement portion having a first position wherein the engagement portion extends into the first bore, the automatic locking mechanism configured to allow movement of the engagement portion in a direction away from the longitudinal axis of the first bore in response to an anchoring pin being inserted into the first bore and forced against the engagement portion.

In one embodiment, a method of distracting vertebrae includes engaging a first vertebra through a first distractor arm, implanting an anchoring pin in a second vertebra, receiving the anchoring pin within a bore in a second distractor arm, moving an engaging portion of a locking arm located within the bore in a direction away from a central axis of the bore, coupling the anchoring pin to the second distractor arm with the engaging portion and moving one of the first distractor arm and the second distractor arm in a direction away from the other of the first distractor arm and the second distractor arm.

The above-described features and advantages, as well as others, will become more readily apparent to those of ordinary skill in the art by reference to the following detailed description and accompanying drawings.

BRIEF DESCRIPTION OF THE DRAWINGS

FIG. 6 shows a partial cross-sectional view of the distractor arm of FIG. 4 with the engagement portion of the locking arm engaging the upper threaded portion of the anchoring pin of FIG. 5 so as to couple the anchoring pin and the distractor;

FIG. 7 shows the partial cross-sectional view of the distractor arm of FIG. 6 with the locking arm pivoted to disengage the engagement portion of the locking arm from the upper threaded portion of the fastener;

FIG. 8 shows a side plan view of an alternative distractor assembly with a sliding locking arm in accordance with principles of the present invention;

FIG. 9 shows a partial cross-sectional view of a distractor arm of the distractor assembly of FIG. 8 taken along the line A-A of FIG. 10 with the locking arm removed;

FIG. 10 shows a cross-sectional view of the distractor arm of the distractor assembly of FIG. 8 with the locking arm biased to a position wherein the engagement portion of the locking arm extends into the internal bore of the distractor arm to couple a pin to the distractor assembly;

FIG. 11 shows a cross-sectional view of the distractor arm of the distractor assembly of FIG. 8 with the locking arm moved to a position wherein the engagement portion of the locking arm no longer extends into the internal bore of the distractor arm;

FIG. 12 is a front plan view of an alternative distractor assembly with a pivoting locking arm in accordance with principles of the present invention;

FIG. 13 shows a partial cross-sectional view of a distractor arm of the distractor assembly of FIG. 12 showing the engagement portion of a locking arm extending into the internal bore of the distractor arm;

FIG. 14 shows a top plan view of the locking arm of the distractor assembly of FIG. 12;

FIG. 15 shows a side plan view of the locking arm of the distractor assembly of FIG. 12;

FIG. 16 shows a partial cross-sectional view of the distractor arm of the distractor assembly of FIG. 12 with the locking arm biased to a position wherein the engagement sections of the locking arm extend into the internal bore of the distractor arm to block the path of a pin received into the distractor assembly;

FIG. 17 shows a top cross-sectional view of the distractor arm of the distractor assembly of FIG. 12 with the locking arm biased to a position wherein the engagement sections of the locking arm extend into the internal bore of the distractor arm to clamp a pin received into the distractor assembly;

FIG. 18 shows a partial side cross-sectional view of the distractor arm of the distractor assembly of FIG. 12 with the locking arm biased to a position wherein the engagement sections of the locking arm extend into the internal bore of the distractor arm to clamp a pin received into the distractor assembly;

FIG. 19 shows a partial side cross-sectional view of the distractor arm of the distractor assembly of FIG. 12 with the locking arm biased to a position wherein the engagement sections of the locking arm do not extend into the internal bore of the distractor arm, allowing a pin received into the distractor assembly to be removed from the distractor assembly; and FIG. 20 shows a top cross-sectional view of the distractor arm of the distractor assembly of FIG. 12 with the locking arm biased to a position wherein the engagement sections of the locking arm do not extend into the internal bore of the distractor arm, allowing a pin received into the distractor assembly to be removed from the distractor assembly.

FIG. 21 shows a perspective view of an alternative distractor arm with a pivoting locking arm in accordance with principles of the present invention;

FIG. 22 shows a cross-sectional view of the distractor arm of FIG. 21 with the locking arm biased to a position wherein the engagement sections of the locking arm do not extend into the internal bore of the distractor arm, allowing a pin received into the distractor assembly to be removed from the distractor assembly;

FIG. 23 shows a top plan view of the locking arm shown with the distractor arm of FIG. 21;

FIG. 24 shows a cross-sectional view of the distractor arm of FIG. 21 with the locking arm biased to a position wherein the engagement sections of the locking arm extend into the internal bore of the distractor arm to block the path of a pin received into the distractor assembly;

FIG. 25 shows a partial cross-sectional view of an alternative distractor arm with a pin locking mechanism that includes two engaging portions located at different heights of the internal bore of the guide portion of the distractor arm and at generally opposing sides of the internal bore in accordance with principles of the present invention;

FIG. 26 shows a partial cross-sectional view of the distractor arm of FIG. 25 with an anchoring pin inserted in the internal bore such that a coupling portion of the pin is located adjacent to each of the engaging portions of the distractor arm; and FIG. 27 shows a partial cross-sectional view of the distractor arm of FIG. 25 with the anchoring pin coupled to the distractor arm by the rotation of the guide portion of the distractor arm with respect to the anchoring pin.

DETAILED DESCRIPTION

Figure 1:
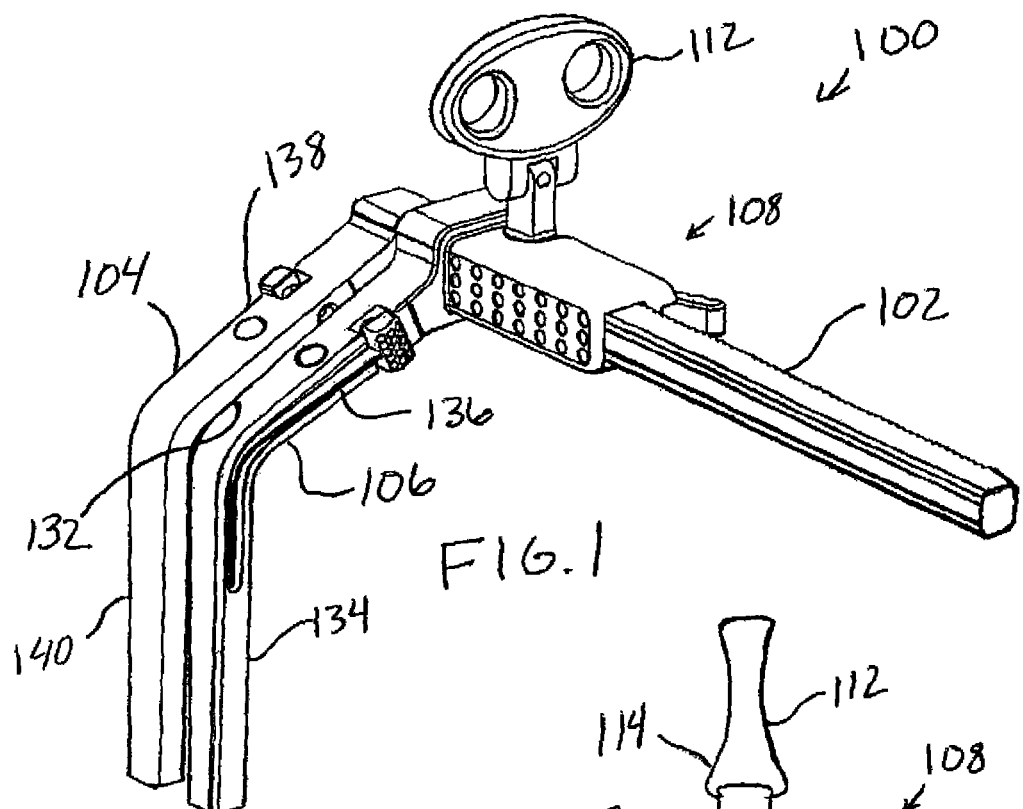
FIG. 1 shows a perspective view of a distractor with a locking arm extending outwardly from a guide portion of a locking arm in accordance with principles of the present invention.

FIG. 1 depicts a distractor assembly 100 which includes a crossbar 102. Two distractor arms 104 and 106 are coupled to the crossbar 102. In this embodiment, the distractor arm 104 is fixedly coupled to the crossbar 102. The distractor arm 106 is movably coupled to the crossbar 102 by a securing mechanism 108. In an alternative embodiment, both distractor arms may be movably coupled to the crossbar.

Figure 2:
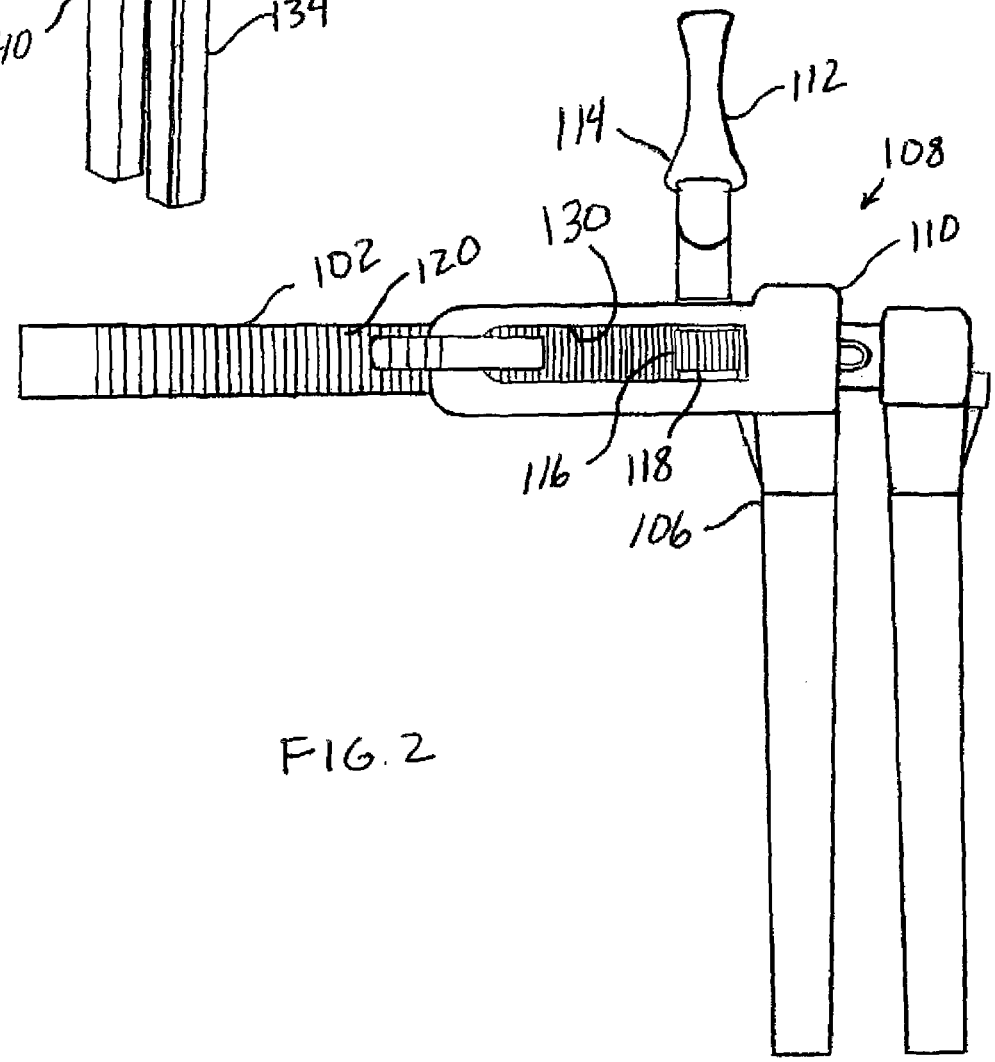
FIG. 2 shows rear plan view of the ratchet-type securing mechanism of the distractor of FIG. 1.

The securing mechanism 108 is a ratchet type system. Referring to FIG. 2, the securing mechanism 108 includes a housing 110 which is attached to the distractor arm 106 and through which the crossbar 102 extends. A thumb screw 112 has a thumb handle 114 and teeth 116 which are located on a cylinder 118. The teeth 116 engage teeth 120 on the crossbar 102.

Figure 3:
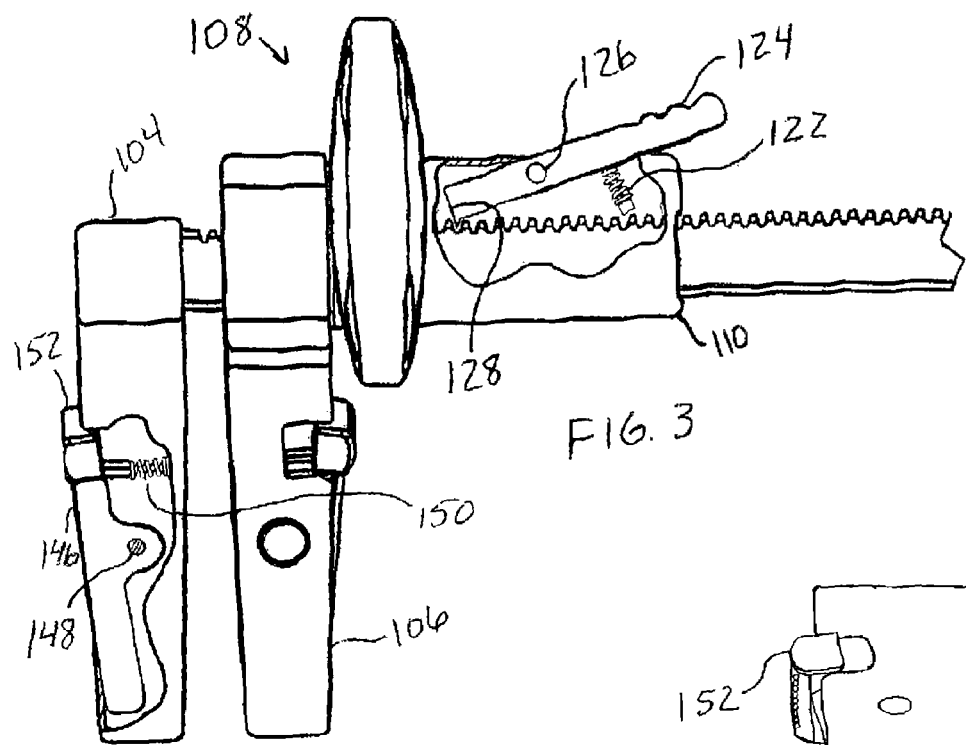
FIG. 3 shows a top partial cutaway view of the securing mechanism and a pivot and biasing member associated with a locking arm of the distractor of FIG. 1.

As shown in FIG. 3, the securing mechanism 108 includes a spring 122 and a lever arm 124. The lever arm 124 is rotatably attached to a pivot 126 and includes an end portion 128. In operation, the spring 122 biases the lever arm 124 in a counterclockwise direction, as viewed in FIG. 3, about the pivot 126. Accordingly, the end portion 128 of the lever arm 124 engages the teeth 120 through an aperture 130 in the housing 110. (See FIG. 2). In other embodiments, clamps, threaded connectors, or pins may be used in place of or in addition to the securing mechanism 108.

Figure 4:
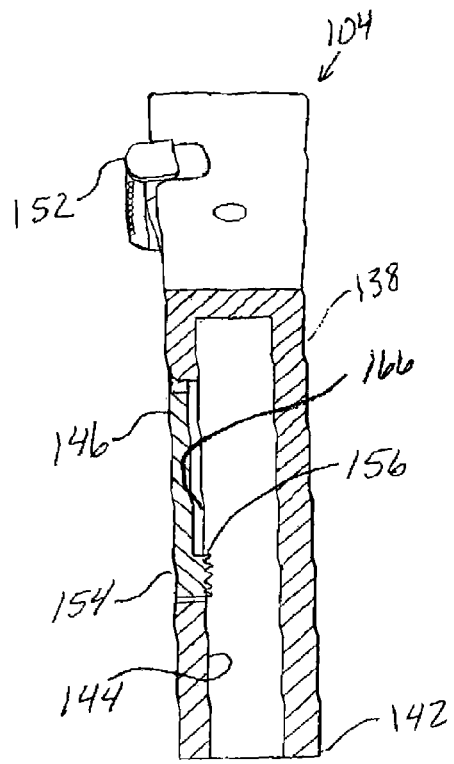
FIG. 4 shows a cross-sectional view of an engagement portion of a locking arm extending into an internal bore of a distractor arm of the distractor of FIG. 1.

Referring now to FIGS. 1-4, the distractor arm 106 includes a housing 132 which includes a guide portion 134 and a slot 136. The distractor arm 104 similarly includes a housing 138 with a guide portion 140 and a slot 166 (see FIG. 4). The bottom 142 of the housing 138 opens to an internal bore 144 shown in FIG. 4. A locking arm 146 is pivotably coupled to the distractor arm 104 through a pivot 148. A biasing member 150 acts upon the locking arm 146 such that the locking arm 146 is biased toward a position wherein a trigger portion 152 of the locking arm 146 extends outwardly from the distractor arm 104 through the slot 166 while an engaging portion 154 at the opposite end of the locking arm 146 extends into the internal bore 144 as shown in FIG. 4. The engaging portion 154 includes a partially threaded section 156.

Figure 5:
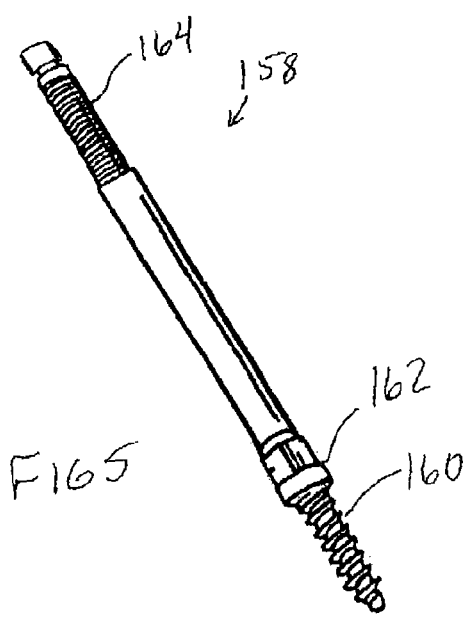
FIG. 5 shows a perspective view of a fastener which may be used in a system incorporating principles of the present invention.

The distractor assembly 100 is configured to be used with an anchoring pin such as pin 158 shown in FIG. 5. The anchoring pin 158 includes a lower threaded portion 160, a flange 162 and an upper threaded portion 164. The lower threaded portion 160 is configured to couple with a bone such as a vertebra while the flange 162 limits the extent to which the pin 158 may be inserted into the bone. The upper threaded portion 164 is sized to fit within the internal bore 144. Additionally, the upper threaded portion 164 and the partially threaded section 156 of the locking arm 146 are complimentarily formed. In alternative embodiments, a distractor system may include other types of fasteners.

In operation, two pins 158 from a distractor system are implanted into adjacent vertebrae in accordance with known methods. The distractor assembly 100 is then adjusted so that the spacing between the distractor arms 104 and 106 is complementary to the spacing between the implanted pins 158. This is accomplished by rotating the thumb handle 114 of the thumb screw 112 in the clockwise direction when viewed from above as shown in FIG. 3. Rotation of the thumb handle 114 causes the cylinder 118 to rotate. Accordingly, because the teeth 116 on the cylinder 118 are engaged with the teeth 120 on the crossbar 102, the securing mechanism 108 and the distractor arm 106 are forced to the right as viewed in FIG. 3.

Continuing with FIG. 3, as the securing mechanism 108 is forced to the right the end portion 128 of the lever arm 124 is forced against the teeth 120. The end portion 128 and the teeth 120 are configured such that when pressure is applied in this direction, the end portion 128 rides up on the teeth 120 thereby compressing the spring 122 as the lever arm 124 pivots about the pivot 126. This continues until the end portion 128 is no longer engaged with the teeth 120. Thus, movement to the right as viewed in FIG. 3 is allowed. In the event the distractor arms 104 and 106 are spaced too widely, however, rotation of the thumb screw 112 is not allowed while the end portion 128 is engaged with the teeth 120.

Specifically, the teeth 120 and the end portion 128 are configured such that a force acting upon the housing 110 toward the left as viewed in FIG. 3 causes the end portion 128 to more firmly engage the teeth 120. Therefore, to move the distractor arm 106 to the left, the spring 122 must first be depressed by applying pressure on the end of the lever 124 opposite the end portion 128. This results in the lever arm 124 pivoting about the pivot 126, thereby disengaging the end portion 128 from the teeth 120.

Once the distractor arms 104 and 106 are properly spaced, the distractor arms 104 and 106 are placed onto the pins 158. With reference to distractor arm 104, as the pins 158 are axially received into the guide portions 140 and 134, the upper threaded portion 164 of the pin 158 contacts the partially threaded portion 156. The partially threaded portion 156 and the upper threaded portion 164 are configured such that as such pressure is applied, the upper threaded portion 164 rides up on the partially threaded portion 156 thereby forcing the engaging portion 154 in a direction away from the internal bore 144. This results in compression of the biasing member 150 as the locking arm 146 pivots about the pivot 148. This continues until the engaging portion 154 is no longer engaged with the upper threaded portion 164. Thus, the pin 158 is allowed to move upwardly within the internal bore 144 until the flange 162 abuts the bottom 142 of the housing 138 as shown in FIG. 6.

When the flange 162 abuts the bottom 142, or when the pin 158 is at the desired location within the internal bore 144, the upper threaded portion 164 of the anchoring pin 158 is engaged with the partially threaded portion 156 of the engaging portion 154 which extends into the internal bore 144 as shown in FIG. 6. The upper threaded portion 164 and the partially threaded portion 156 are configured such that when engaged, a force applied to the distractor arm 104 in the upward direction as shown in FIG. 6 causes the upper threaded portion 164 and the partially threaded portion 156 to become more fully engaged. Likewise, a force applied to the pin 158 in the downward direction as shown in FIG. 6 causes the upper threaded portion 164 and the partially threaded portion 156 to become more fully engaged. Thus, the pin 158 is coupled to the distractor arm 104. The distractor arm 106 is manipulated in a like manner to couple with a pin 158.

Accordingly, as the distractor 100 is used to distract the adjacent bones, the distractor arm 104 is not allowed to translate upwardly along the longitudinal axis of the pin 158. Therefore, the pin 158 and the distractor arm 104 are not allowed to separate.

When the operator chooses to remove the distractor 100 from the pins 158, pressure is applied to the trigger portion 152 thereby causing the biasing member 150 to compress. As the trigger portion 152 compresses the biasing member 150, the trigger portion 152 moves toward the housing 138. This movement causes the locking arm 146 to pivot about the pivot 148. Thus, the engaging portion 154 moves away from the internal bore 144 causing the partially threaded portion 156 to disengage from the upper threaded portion 164 of the pin 158 as shown in FIG. 7. The distractor arm 106 is operated in a like manner. The distractor 100 may then be removed from the pins 158. The locking mechanism of the distractor assembly 100 is thus a type of ratcheting mechanism.

Referring now to FIG. 8, distractor assembly 170 may also be used with a pin 158. The distractor assembly 170 includes a crossbar 172, a fixed distractor arm 174 and a movable distractor arm (not shown). In this embodiment, a locking arm 176 extends out of the guide portion 178 of the distractor arm 174. The guide portion 178 includes an internal bore 180 which is shown in FIG. 9. FIG. 9 is a partial cross-sectional view taken along line A-A of FIG. 10 showing only the guide portion 178.

As shown in FIGS. 9 and 10, two openings 182 and 184 extend from the internal bore 180 completely through the guide portion 178. The openings 182 and 184 join with a pocket 186. The locking arm 176 includes two extensions 188 and 190 which extend from a trigger portion 192 through the openings 182 and 184, respectively, to an engaging portion 194. The engaging portion 194 is configured complementarily to the pocket 186. A biasing member 196 extends between a biasing member pocket 198 in the guide portion 178 and the trigger portion 192. The biasing member 196 biases the locking arm 176 to the left as viewed in FIG. 10. Thus, when no other forces are exerted on the locking arm 176, the engaging portion 194 is positioned partially within the internal bore 180.

In operation, the distractor assembly 170 may be used in a manner similar to the manner described with respect to the distractor assembly 100. The manner in which operation of the distractor assembly 170 differs from that of the distractor assembly 100 is explained with reference to FIGS. 10 and 11. As the pin 158 is received into the internal bore 180, the upper threaded portion 164 of the pin 158 contacts the engaging portion 194. The partially threaded portion 156 and the engaging portion 194 are configured such that as pressure is applied in this direction, the upper threaded portion 164 rides up on the engaging portion 194 thereby forcing the engaging portion 194 in a direction away from the internal bore 180. This results in compression of the biasing member 196 as the engaging portion 194 is moved into the pocket 186. When the engaging portion 194 has been moved to the position shown in FIG. 11, the engaging portion 194 no longer blocks the movement of the pin 158. Thus, the pin 158 is allowed to move upwardly within the internal bore 180 until the flange 162 abuts the housing distractor arm 174.

Once the upward movement of the pin 158 within the internal bore 180 is stopped, the upper threaded portion 164 no longer acts to force the engaging portion 194 into the pocket 186. Accordingly, the biasing member 196 acts upon the locking arm 192 to move the locking arm to the left as viewed in FIGS. 9 and 10. Thus, the engaging portion 194 is moved into the internal bore 180 to the position shown in FIG. 10. As shown in FIG. 10, the engaging portion 194 has engaged the upper threaded portion 164 of the pin 158. To this end, the engaging portion 104 may include a partially threaded section similar to that of the engaging portion 154.

The upper threaded portion 164 and the engaging portion 194 are configured such that when engaged, a force applied to the distractor arm 174 in the upward direction as shown in FIG. 8 causes the upper threaded portion 164 and the engaging portion 194 to become more fully engaged. Likewise, a force applied to the pin 158 so as to move the pin 158 out of the internal bore 180 causes the upper threaded portion 164 and the partially threaded portion 156 to become more fully engaged. Thus, the pin 158 is coupled to the distractor arm 174. Accordingly, as the distractor 170 is used to distract adjacent bones, the distractor arm 174 is not allowed to translate along the longitudinal axis of the pin 158. Therefore, the pin 158 and the distractor arm 174 are not allowed to separate.

When the operator chooses to remove the distractor 170 from the pin 158, pressure is applied to the trigger portion 192 thereby causing the biasing member 196 to compress. As the trigger portion 192 compresses the biasing member 196, the trigger portion 192 moves toward the distractor arm 174. This movement causes the extensions 188 and 190 to move within the openings 182 and 184. Thus, the engaging portion 94 moves away from the internal bore 180 and into the pocket 186 as shown in FIG. 11. The distractor arm 174 may then be removed from the pin 158. The locking mechanism of the distractor assembly 170 is thus a type of ratcheting mechanism.

Referring now to FIG. 12, an alternative embodiment of a distractor assembly in accordance with principles of the present invention is shown. The distractor assembly 200 includes a crossbar 202, a fixed distractor arm 204 and a movable distractor arm (not shown). In this embodiment, the crossbar 202 is configured as a lordodic rack. A locking arm 206 extends out of the guide portion 208 of the distractor arm 204. The guide portion 208 includes an internal bore 210 which is shown in FIG. 13. A cavity 212 is located at one side of the internal bore 210 and a cavity 214 is located generally opposite the cavity 212. The placement of the locking arm 206 with respect to the guide portion 208, like the placement of the locking arms in the other disclosed embodiments, may be modified if desired.

Referring to FIGS. 14 and 15, the locking arm 206 includes a trigger portion 216, two extensions 218 and 220, an engaging portion 222, and a base section 224. The base section 224 includes a neck 226 and a tab 228. The tab 228 is configured to be coupled to the guide portion 208 while the neck 226 is configured to provide a shape retaining connection between the tab 228 and the rest of the locking arm 206 and to be more flexible than the rest of the locking arm 206.

The engaging portion 222 defines an opening 230 which is somewhat oblong. Two engaging sections 232 and 234 are located at opposing ends of the opening 230. When the locking arm 206 is assembled into the guide section 208, the two extensions 218 and 220 pass through two slots 236 (best seen in FIGS. 17) and 238 (best seen in FIG. 12) in the guide portion 208 and into the cavity 212. In the position shown in FIG. 13, the engaging sections 232 and 234 extend into the internal bore 210 and the neck 226 is located in the cavity 214.

In operation, the distractor assembly 200 may be used in a manner similar to the manner described with respect to the distractor assembly 100. The manner in which operation of the distractor assembly 200 differs from that of the distractor assembly 100 is explained with reference to FIGS. 16-20. In this example, a pin 240 is used with the distractor assembly 200. The pin 240 in this example has a smooth upper shaft. Alternatively, the distractor assembly 200 may be used with pins having a tapered or threaded upper shaft. In either embodiment, the hole 230 is sized so that when the locking arm 206 is in the position shown in FIG. 26, at least one of the engaging sections 232 and 234 extend into the internal bore 210 to a sufficient extent to at least partially block the internal bore 210. Thus, as the pin 240 is axially received into the internal bore 210, the pin 240 contacts either the engaging section 232 or the engaging section 234. For purposes of this example, the pin 240 contacts the engaging section 232 as shown in FIG. 16.

After the pin 240 contacts the engaging section 232, continued application of sufficient pressure will cause the neck 226 to flex, thereby allowing the engaging portion 222 and the extensions 218 and 220 to rotate in the upwardly direction with respect to the view of FIG. 16. Accordingly, the engaging section 232 rotates to a position where less of the internal bore 210 is blocked by the engaging section 232. Likewise, the engaging section 234 rotates to a position where less of the internal bore 210 is blocked by the engaging section 234. Thus, as shown in FIG. 17, the opening of the internal bore 210 is increased such that the minimum diameter of the hole 230 when projected on a plane perpendicular to the longitudinal axis of the pin 240 is sufficient to allow sliding movement between the pin 240 and the engaging sections 232 and 234. This allows the pin 240 to be moved upwardly within the internal bore 210. Thus, so long as the pin 240 is moving upwardly within the internal bore 210, the force exerted on the engaging sections 232 and 234 by the pin 240 is more than the force exerted on the locking arm 206 by the flexed neck 226 allowing for continued sliding movement between the engaging sections 232 and 234 and the pin 240.

The pin 240 may then be moved upwardly into the internal bore 210 until it is in the desired position such as is shown in FIG. 18. FIG. 18 shows both engaging sections 232 and 234 in contact with the pin 240. Additionally, the neck 226 is flexed, thereby providing a torque on the engaging portion 222 in the counterclockwise direction. The neck 226 thus provides a force which clamps the pin 240 between the engaging sections 232 and 234 once the upward force on the pin 240 is less than the force exerted by the neck 236. Moreover, any force applied to the distractor 200 or the pin 240 in a direction tending to move the pin 240 out of the internal bore 210 (downwardly) causes additional clamping force to be applied by the engaging sections 232 and 234 on the pin 240. The pin 240 is thus coupled to the guide section 208 through the locking arm 206. Accordingly, as the distractor 200 is used to distract adjacent bones, the distractor arm 204 is not allowed to translate upwardly along the longitudinal axis of the pin 240. Therefore, the pin 240 and the distractor arm 200 are not allowed to separate.

When the operator chooses to remove the distractor 200 from the pin 240, pressure is applied to the trigger portion 216 in the direction of the arrow 242 shown in FIG. 18. The force on the trigger portion 216 is passed through the extensions 218 and 220 through the engagement portion 22 to the neck 226 thereby causing the neck 226 to flex. As the neck 226 flexes, the extensions 218 and 220, the engagement portion 222 and the trigger portion 216 are allowed to rotate in the direction of the arrow 242.

Accordingly, the engaging section 232 rotates to a position where less of the internal bore 210 is blocked by the engaging section 232. Likewise, the engaging section 234 rotates to a position where less of the internal bore 210 is blocked by the engaging section 234. When the locking arm 206 has rotated to the position shown in FIG. 19, the opening of the internal bore 210 is increased such that the minimum diameter of the hole 230 when projected on a plane perpendicular to the longitudinal axis of the pin 240 is larger than the diameter of the pin 240. Thus, the distractor arm 204 may be separated from the pin 240. The locking mechanism of the distractor assembly 200 is thus a type of ratcheting mechanism which uses friction to couple a pin to the distractor assembly 200. Accordingly, the engagement sections 232 and 234 and/or the pin used with the distractor assembly 200 may incorporate surface textures or materials to increase the ability of the engagement sections 232 and 234 to clamp the pin.

Referring now to FIG. 21, an alternative embodiment of a distractor arm in accordance with principles of the present invention is shown. The distractor arm 250 includes a coupling portion 252 for coupling with a crossbar (not shown). A locking arm 254 extends out of the guide portion 256 of the distractor arm 250. The guide portion 256 includes an internal bore 258 which is shown in FIG. 22. A cavity 260 is located within the internal bore 258.

Referring to FIG. 23, the locking arm 254 includes a trigger portion 262, an extension 264, an engaging portion 266, and a base section 268 which is similar to the base section 224. The engaging portion 266 defines an opening 270 which is somewhat oblong. Two engaging sections 272 and 274 are located at opposing ends of the opening 270. When the locking arm 250 is assembled into the guide section 256, the extension 264 passes through a slot 276 in the guide portion 256 and into the cavity 260. In the position shown in FIGS. 21 and 24, the engaging sections 272 and 274 extend into the internal bore 258.

The operation of the locking mechanism in the distractor arm 250 is similar to the operation of the locking mechanism discussed above with respect to the distractor assembly 200. In brief, as the trigger portion 262 is rotated from the position shown in FIGS. 21 and 24 in the upward direction as indicated by the arrow 278 in FIG. 21, the engaging sections 272 and 274 rotate so as to move outwardly from the center of the internal bore 258. The main difference between the locking mechanism in the distractor arm 250 and the locking mechanism discussed above with respect to the distractor assembly 200 is that the hole 270 is in the shape of a rectangle. Thus, the locking arm 254 may be used with an anchoring pin (not shown) with a rectangular coupling portion. This allows the anchoring pin to be gripped by the engaging sections 272 and 274 along an entire side of the shaft of the anchoring pin. Moreover, the locking arm 254 may be used with anchoring pins having coupling portions configured in other shapes, including circular shapes, and with or without threads.

Referring now to FIG. 25, an alternative embodiment of a distractor arm in accordance with principles of the present invention is shown. The distractor arm 280 includes a coupling portion (not shown) for coupling with a crossbar (not shown). A guide portion 282 includes an internal bore 284 which extends axially within the guide portion 282 from the bottom 286 of the guide portion 282. The internal bore 284 includes a first threaded portion 288 and a second threaded portion 290.

The distractor arm 280 is configured in this embodiment to be used with an anchoring pin 292. The anchoring pin 292 includes an upper threaded portion 294 and a lower threaded portion 296. The upper threaded portion 294 and the lower threaded portion 296 extend completely around the anchoring pin 292 and are separated by a smooth shank portion 298. In an alternative embodiment, the threaded portions of the anchoring pin are not separated by a smooth portion. In a further embodiment, the threaded portions do not extend completely around the anchoring pin.

In operation, a distractor system incorporating the distractor arm 280 and the anchoring pin 292 may be initially positioned in the manner described above. The internal bore 284 is sized to allow the anchoring pin 292 to fit within the internal bore 284. In this embodiment, the internal bore 284 is circular. In alternative embodiments, the internal bore may be oblong, rectangular, or another desired shape. After the distractor arm 280 is axially aligned with the anchoring pin 292, the anchoring pin 292 is axially received into the internal bore 284 by moving the distractor arm in the direction of the arrow 300 in FIG. 25. The movement of the distractor arm 280 in the direction of the arrow 300 continues until the anchoring pin 292 is positioned as shown in FIG. 26. In FIG. 26, the upper threaded portion 294 is adjacent to the first threaded portion 288 and the lower threaded portion 296 is adjacent to the second threaded portion 290.

In the condition of FIG. 26, the anchoring pin 292 is axially received within the internal bore 284, but the anchoring pin 292 is not coupled to the guide portion 282. As the distractor is manipulated so as to separate, for example, two vertebrae, a force is applied to the distractor arm 280 which forces the guide portion 282 in the direction of the arrow 302 shown in FIG. 26. Because the anchoring pin 292 is implanted in a bone, a torque is created about the pin 292 causing the guide portion 282 to rotate in the direction of the arrow 304 to the position shown in FIG. 27.

In FIG. 27, the rotation of the guide portion 282 with respect to the anchoring pin 292 causes the upper threaded portion 294 to engage the first threaded portion 288 and the lower threaded portion 296 to engage the second threaded portion 290. Accordingly, the anchoring pin 292 is coupled to the guide portion 4284 by the first threaded portion 288 and the second threaded portion 290 which, in this embodiment, are parts of a locking mechanism. Removal of the distractor arm 280 from the anchoring pin 292 is accomplished by moving the distractor arm 280 along the cross bar in the direction of the arrow 306. As the distractor arm 280 is moved in this manner, the guide portion 280 will rotate in the direction of the arrow 308 to the position shown in FIG. 26, allowing the distractor arm 280 to be removed from the anchoring pin 292.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. By way of example, the present invention may be used with a variety of fasteners and with a variety of crossbars in addition to those described above. The invention in its broadest aspects is therefore not limited to the specific details, implementations, or illustrative examples shown and described. Accordingly, departures may be made from such details without departing from the spirit or scope of applicant's general inventive concept.

We claim:

1. A method of distracting vertebrae comprising:
engaging a first vertebra through a first distractor arm;
implanting an anchoring pin in a second vertebra;
receiving the anchoring pin within a bore in a second distractor arm;
moving an engaging portion of a locking arm, the engaging portion located within the bore, in a direction away from a central axis of the bore as the anchoring pin is being received within the bore;
coupling the anchoring pin to the second distractor arm with the engaging portion; and
moving one of the first distractor arm and the second distractor arm in a direction away from the other of the first distractor arm and the second distractor arm.

2. The method of claim 1, wherein moving the engaging portion comprises:
contacting the engaging portion of the locking arm within the bore with the anchoring pin so as to move the engaging portion in a direction away from the central axis of the bore.

3. The method of claim 2, wherein contacting the engaging portion comprises:
rotating the engaging portion of the locking arm away from the central axis of the bore.

4. The method of claim 1, wherein moving the engaging portion comprises:
moving the engaging portion of the locking arm linearly away from the central axis of the bore.

5. The method of claim 1 wherein moving the engaging portion comprises:
pivoting the locking arm about a pivot located between the engaging portion and a trigger portion of the locking arm.

6. The method of claim 1 wherein moving the engaging portion comprises:
rotating a trigger portion of the locking arm about a first arc; and
rotating the engaging portion of the locking arm about a second arc, wherein the length of the first arc is greater than the length of the second arc.

7. The method of claim 1, wherein coupling the anchoring pin comprises:
clamping a portion of the anchoring pin between a first engagement section of the engagement portion and a second engagement section of the engagement portion.

8. The method of claim 1, wherein coupling the anchoring pin comprises:
engaging a threaded portion of the anchoring pin with a threaded portion of the engagement portion.

* * * * *